(12) United States Patent
Ewing et al.

(10) Patent No.: US 9,182,320 B2
(45) Date of Patent: Nov. 10, 2015

(54) SYSTEM APPARATUS AND METHOD OF SAMPLING A BROAD RANGE OF CHEMICALS (SBRC) BY COLLECTION AND ANALYSIS OF CHEMICAL VAPORS AEROSOLS PARTICULATES AND LIQUID DROPLETS ON SURFACES

(71) Applicants: Kenneth J. Ewing, Edgewood, MD (US); Daniel J. Gibson, Cheverly, MD (US); Jasbinder S. Sanghera, Ashburn, VA (US); Robert E. Miklos, La Plata, MD (US)

(72) Inventors: Kenneth J. Ewing, Edgewood, MD (US); Daniel J. Gibson, Cheverly, MD (US); Jasbinder S. Sanghera, Ashburn, VA (US); Robert E. Miklos, La Plata, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 331 days.

(21) Appl. No.: 13/930,627

(22) Filed: Jun. 28, 2013

(65) Prior Publication Data
US 2014/0260693 A1 Sep. 18, 2014

Related U.S. Application Data

(60) Provisional application No. 61/790,457, filed on Mar. 15, 2013.

(51) Int. Cl.
*G01N 1/24* (2006.01)
*G01N 1/22* (2006.01)
*G01N 1/02* (2006.01)

(52) U.S. Cl.
CPC .............. *G01N 1/2205* (2013.01); *G01N 1/24* (2013.01); *G01N 2001/022* (2013.01); *G01N 2001/245* (2013.01)

(58) Field of Classification Search
CPC .......................... G01N 1/24; G01N 2001/245
USPC .............................. 73/864.71, 836.21, 836.23
See application file for complete search history.

(56) References Cited

U.S. PATENT DOCUMENTS

| | | | | |
|---|---|---|---|---|
| 4,576,054 A * | 3/1986 | Lalin | .......................... | 73/863.03 |
| 5,321,984 A * | 6/1994 | Stroupe | ..................... | 73/863.11 |
| 5,553,508 A * | 9/1996 | Dabberdt et al. | .......... | 73/863.02 |
| 5,693,895 A * | 12/1997 | Baxter | ....................... | 73/863.22 |
| 5,717,147 A * | 2/1998 | Basch et al. | ............... | 73/863.23 |
| 6,354,160 B1 * | 3/2002 | Staples et al. | .............. | 73/863.12 |
| 7,299,709 B1 | 11/2007 | Grove et al. | | |
| 2002/0134173 A1 * | 9/2002 | Lindgren et al. | ........... | 73/863.11 |

(Continued)

*Primary Examiner* — Laura Martin
*Assistant Examiner* — Herbert K Roberts
(74) *Attorney, Agent, or Firm* — US Naval Research Laboratory; L. George Legg

(57) ABSTRACT

Sampling of a broad range of chemicals using a handheld sampler body, having a sample screen in a sampling cassette; where a sample screen housing further consists of a locking arm arrestor body, where, the locking arm arrestor body including a draw tube, and where the sampling screen can be positioned in either a retracted or extended positioned regarding a sample access face. When activated, the system executes collecting and sampling operations of chemicals, by exposing the extended sampling screen to a sampling environment, drawing through the draw tube, air from the sampling environment, further collecting, onto the surface of the sample screen solid particles and/or pressing the sample screen against the surface(s) of object in the sampling environment. Then, removing the sampling screen from the sampling environment and isolating the plurality of airborne chemical contaminants, by retracting a sample screen into the sample screen housing.

20 Claims, 17 Drawing Sheets

(56) References Cited

U.S. PATENT DOCUMENTS

| | | |
|---|---|---|
| 2002/0148305 A1* | 10/2002 | Danylewych-May et al. .................. 73/863.21 |
| 2004/0016308 A1* | 1/2004 | Rogers et al. .............. 73/863.25 |
| 2004/0069047 A1* | 4/2004 | Coyle et al. ................. 73/28.04 |
| 2005/0081655 A1* | 4/2005 | Fine et al. .................. 73/864.71 |
| 2006/0123931 A1* | 6/2006 | Wareham et al. .......... 73/864.71 |
| 2007/0034024 A1 | 2/2007 | Syage |
| 2008/0245164 A1* | 10/2008 | Chang ........................ 73/864.71 |
| 2009/0266181 A1* | 10/2009 | Peng et al. ................. 73/864.71 |
| 2010/0104473 A1* | 4/2010 | Kirollos et al. ................. 422/58 |

* cited by examiner

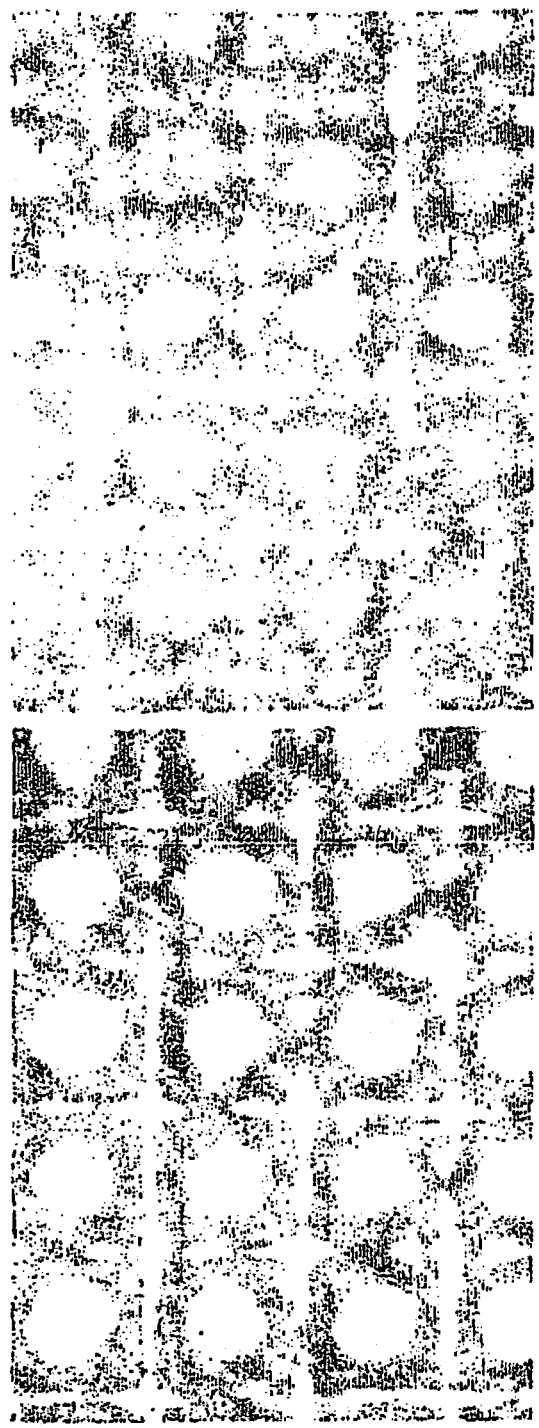

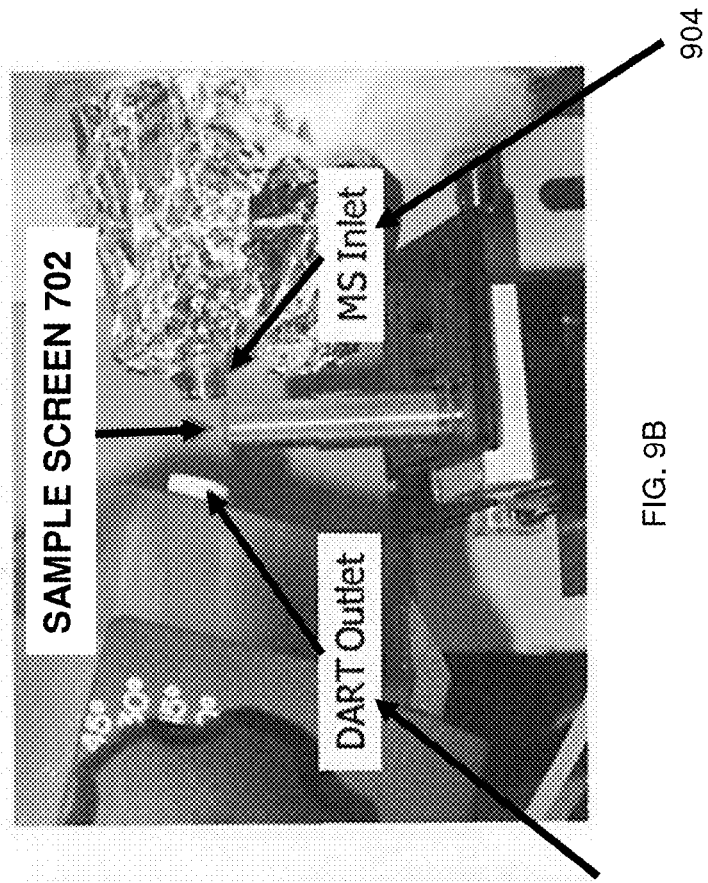
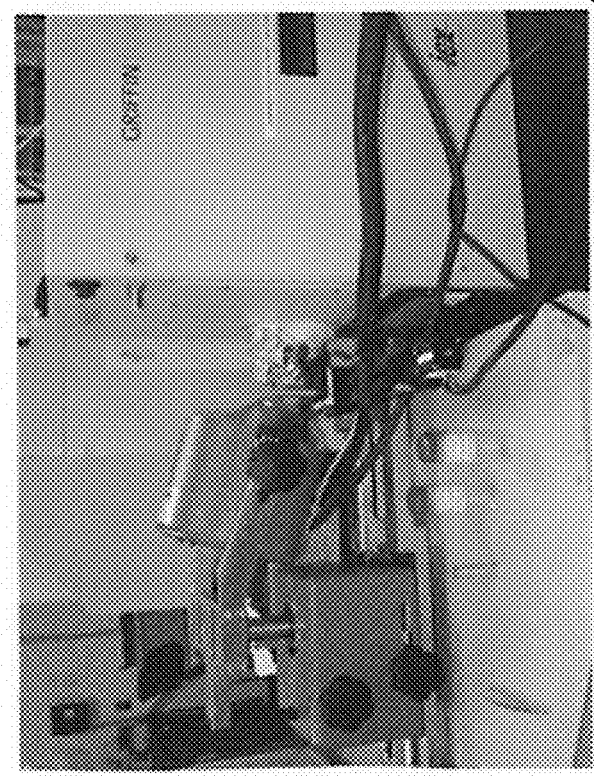
FIG. 9B
FIG. 9A

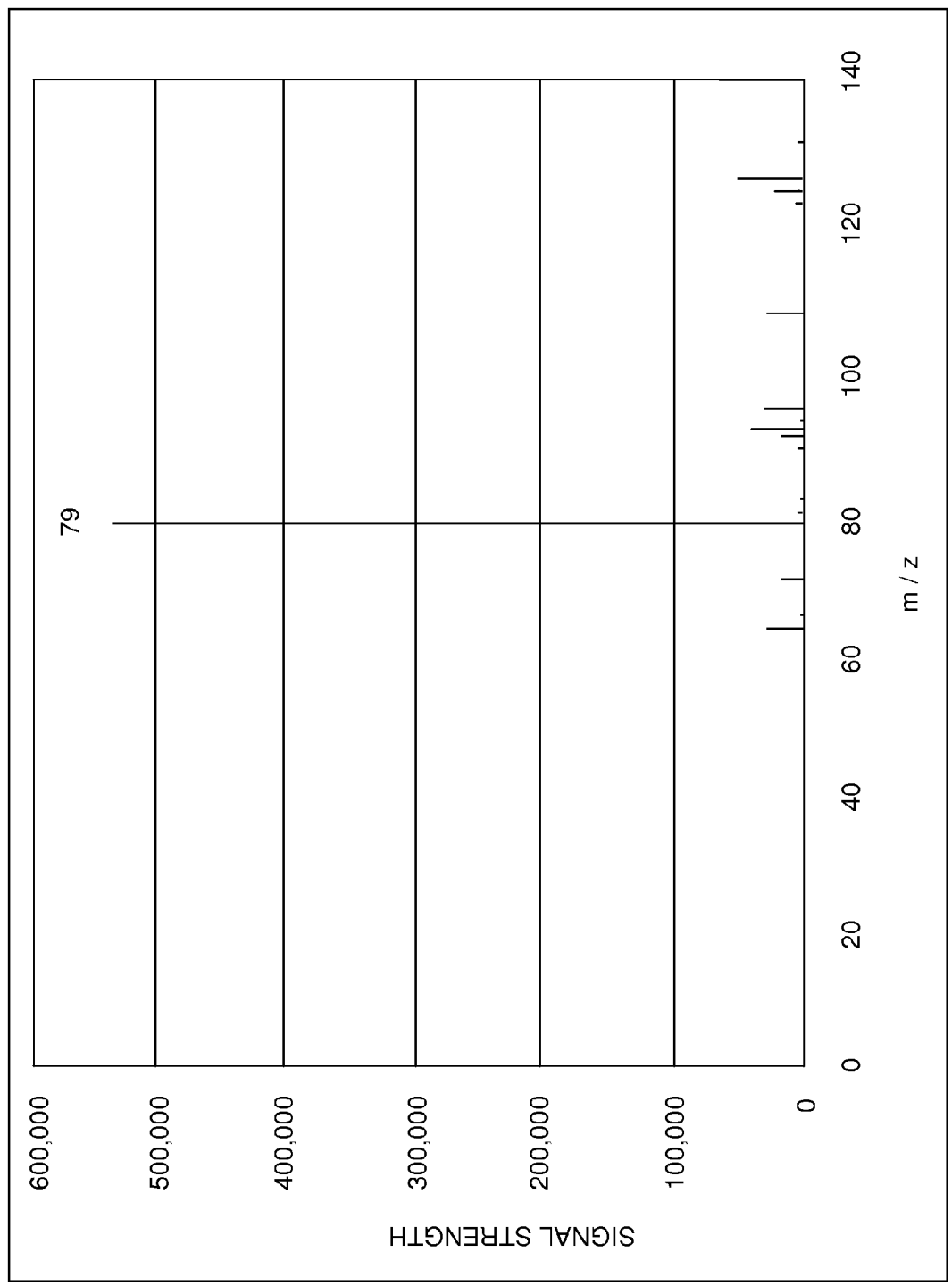

US 9,182,320 B2

SYSTEM APPARATUS AND METHOD OF SAMPLING A BROAD RANGE OF CHEMICALS (SBRC) BY COLLECTION AND ANALYSIS OF CHEMICAL VAPORS AEROSOLS PARTICULATES AND LIQUID DROPLETS ON SURFACES

RELATED APPLICATIONS

The instant U.S. patent application claims the benefit of domestic priority from and is related to U.S. Provisional Patent Application No. 61/790,457; SYSTEM APPARATUS AND METHOD OF SAMPLING A BROAD RANGE OF CHEMICALS (SBRC) BY COLLECTION AND ANALYSIS OF CHEMICAL VAPORS AEROSOLS PARTICULATES AND LIQUID DROPLETS ON SURFACES; filed on Mar. 15, 2013; whose inventors include Kenneth J. Ewing, Daniel J. Gibson Robert E. Miklos, and Jasbinder S. Sanghera; where said U.S. Provisional patent application is herein incorporated by reference in its entirety.

FIELD OF THE INVENTION

The present invention relates to chemical and biological agent collection and detection methods and systems, regarding defense of cities, military installations, forces and assets and civilian personnel against chemical incidents and/or attacks involving chemical toxins, including airborne aerosols and vapors; this invention can also be applied to ambient aerosol particles or pollutants and/or contaminants. More particularly, the present invention enables collection of a broad range of chemicals at sub-toxic levels, including Low Vapor Pressure Chemicals (LVPCs) as chemical aerosols and solid and liquid particulates on surfaces and chemical vapors of more volatile chemicals using the same sampling format.

BACKGROUND OF THE INVENTION

Toxic chemicals can be effective at very low concentrations and are usually colorless and odorless in the form of gas or vapors. Some toxic chemicals can be classified as non-persistent and their effects drop off after hours or minutes.

Other toxic chemicals can be classified as persistent and have a relative low vapor pressure and are usually delivered as liquid droplet particles or aerosols. Their effects can last for a week or more in such liquid and/or particulate forms.

Low vapor pressure toxic chemicals are recognized as threats by both military and Homeland Security agencies. These chemicals exhibit vapor pressures on the order of $10^{-6}$ to $10^{-8}$ torr, (where, a torr is equal to the pressure required to raise a column of mercury 1 mm) and can exist as either liquid droplets or solid particulates, and present an inhalation threat as an aerosol and a contact threat as surface particulates and/or droplets.

Sorbent tubes have been used for over a decade to collect vapor phase samples as well as solid phase micro-extraction (SPME) fibers. However, neither of these vapor collection technologies is capable of collecting aerosols or particulates on surfaces. Aerosol collection can be performed using either a filter based collector where the aerosols are trapped by the fibrous nature of the filter or a cyclonic type of collector where the different sized particulate samples are concentrated and separated by the use of an air cyclone. Currently particulate samples are collected using specialized wipes that are designed to collect particles from surfaces based on electrostatic attraction between the wipe and the particulates. None of these systems is capable of collecting all forms of target analyte; aerosols, and particulates on surfaces, and vapors in the air, and being easily interfaced with analytical instruments.

Because of their extremely low vapor pressures, low vapor pressure toxic chemicals cannot be detected using state-of-the-art chemical agent detectors, which all require that the sample be in the vapor phase for detection. Therefore, there exists a need for the capability to collect these toxic aerosols and particulates on surfaces as well as the more volatile chemicals existing as vapors using a common collection platform that can be integrated into various chemical agent detectors for ease of delivery of vapors (of the low vapor pressure toxic chemicals) for analysis.

SUMMARY OF THE INVENTION

A system of sampling a broad range of chemicals (SBRC), the system includes a handheld sampler body, having a sample screen sampling face, and at least one sampling cassette; and a sample screen housing residing in the sampling cassette; where, the sample screen housing further consists of a screen storage body, a sample access face, and a locking arm arrestor body, and where, the locking arm arrestor body is composed of a screen mount assembly including a draw tube. The screen mount assembly further consists of a locking arm communicatively coupled to a screen cartridge holder, a standoff spring extendably and retractably coupled to the screen cartridge holder, a sampling screen (also referred to as a "sampling medium" and herein after referred to as a "sample screen"), mounted on the standoff spring, where the sample screen can be positioned in either a retracted position or an extended position in the sampling cassette. The system further comprises a battery 6111, a plurality of fans 6112, and a plurality of electrical motors 6113; and the plurality of fans 6112 and the plurality of electrical motors 6113 are communicatively coupled to and powered by the battery 6111. The system further comprises a plurality of electronic and electrical sampling data collection circuits 6114, and a plurality of electronic and electrical sample chain of custody determination circuits 6115 and a plurality of electronic and electrical data analysis circuits 6116 and input/output interface circuits 6117, (where the battery 6111, the plurality of fans 6112, and the plurality of electrical motors 6113, and the plurality of electronic and electrical sampling data collection circuits 6114, and the plurality of electronic and electrical sample chain of custody determination circuits 6115, and the plurality of electronic and electrical data analysis circuits 6116 and input/output interface circuits 6117 are all part of a system of downstream components 110, which can also include computer processors executing computer program code and/or software instructions), and when activated by an operator, the system executes a plurality of collecting operations and a plurality of sampling operations of the broad range of chemicals, by exposing the sample screen to a sampling environment by extending the screen mount assembly through the sample screen housing and the sample screen sampling face; manipulating the locking arm causing compression of the standoff spring, and positioning the locking arm in a locked position in the locking arm arrestor body, where the screen mount assembly includes the draw tube, and by positioning the locking arm in the locked position, causing the sample screen to be positioned protruding beyond an outside surface of the sample screen face, and drawing through the draw tube, air from the sampling environment containing a plurality of airborne chemical contaminants, causing the plurality of airborne chemical contaminants including aerosol particulates to be collected by and adhered to the sample screen, then pressing, by an operator, the surface of the sample screen against the surface(s) of an object situated in the sampling environment, and further collecting, onto the surface of the sample screen solid particles and/or liquid droplets containing a plurality of particulates from the object's surface. Removing the sample screen from the sampling environment, thus removing the plurality of solid particles and the plurality of liquid droplets containing the plurality of particulates collected from the sampling environment; thereby isolating the plurality of airborne chemical contaminants by retracting the screen mount assembly through the sample screen housing and the sample screen sampling face, inside of the sample screen housing.

BRIEF DESCRIPTION OF THE DRAWINGS

FIG. 8A illustrates a sample screen 702 coated with a sticky substance, before chemical particulates are captured on the sample screen 702.

FIG. 8B illustrates a sample screen 702 coated with a sticky substance and showing chemical particulates captured on the sticky screen.

FIG. 9A illustrates an analysis configuration, where a screen mount assembly 501 is positioned between the Direct Analysis in Real Time (DART) ambient ionization system outlet (i.e., DART Outlet 902) and the mass spectrometer inlet (MS Inlet 904).

FIG. 9B illustrates a close up view of the analysis configuration, where a screen mount assembly 501 is positioned between the Direct Analysis in Real Time (DART) ambient ionization system outlet (i.e., DART Outlet 902) and the mass spectrometer inlet (MS Inlet 904).

FIG. 13A illustrates a mass spectrum graphic of DMMP/SG collected onto a stainless steel sticky screen 104, coated with PDMS.

DETAILED DESCRIPTION

Figure 1:
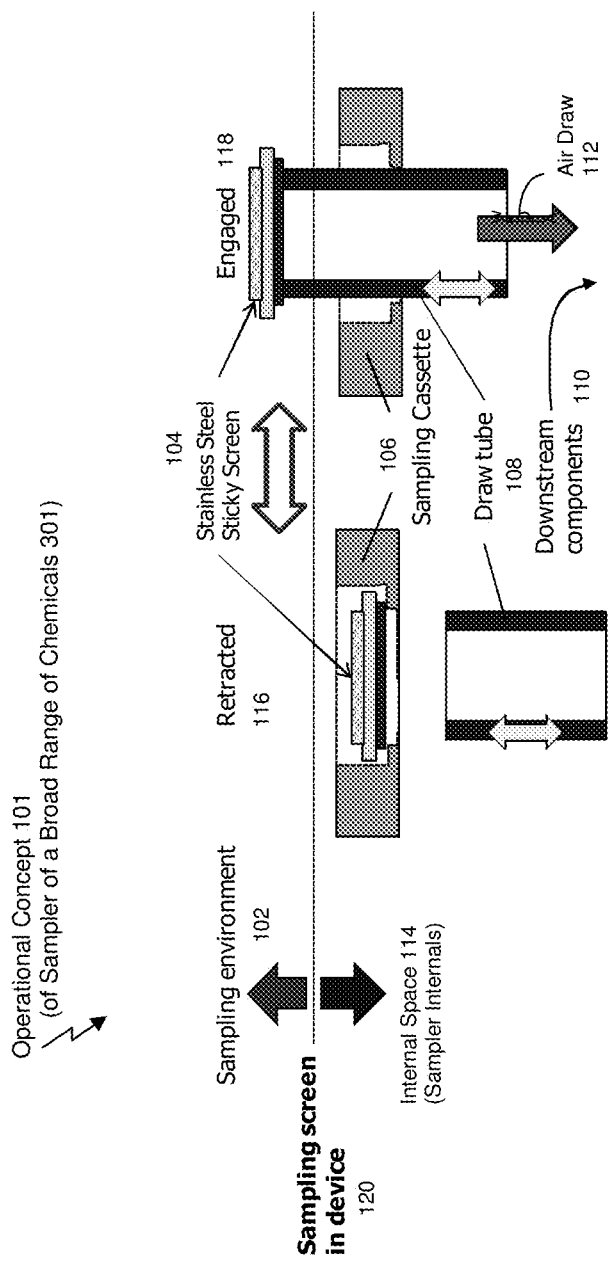
FIG. 1 illustrates a general description of the operational requirements of the collection system for sampling a broad range of chemicals.

Preferred exemplary embodiments of the present invention are now described with reference to the figures, in which like reference numerals are generally used to indicate identical or functionally similar elements. While specific details of the preferred exemplary embodiments are discussed, it should be understood that this is done for illustrative purposes only. A person skilled in the relevant art will recognize that other configurations and arrangements can be used without departing from the spirit and scope of the preferred exemplary embodiments. It will also be apparent to a person skilled in the relevant art that the exemplary embodiments can also be employed in other applications. Further, the terms "a", "an", "first", "second" and "third" etc. used herein do not denote limitations of quantity, but rather denote the presence of one or more of the referenced items(s).

FIG. 1 describes a sampler of a broad range of chemicals consisting of an internal space which is isolated from the ambient environment such that chemical aerosols and vapors cannot penetrate into the internal space of the sampler.

Figure 2:
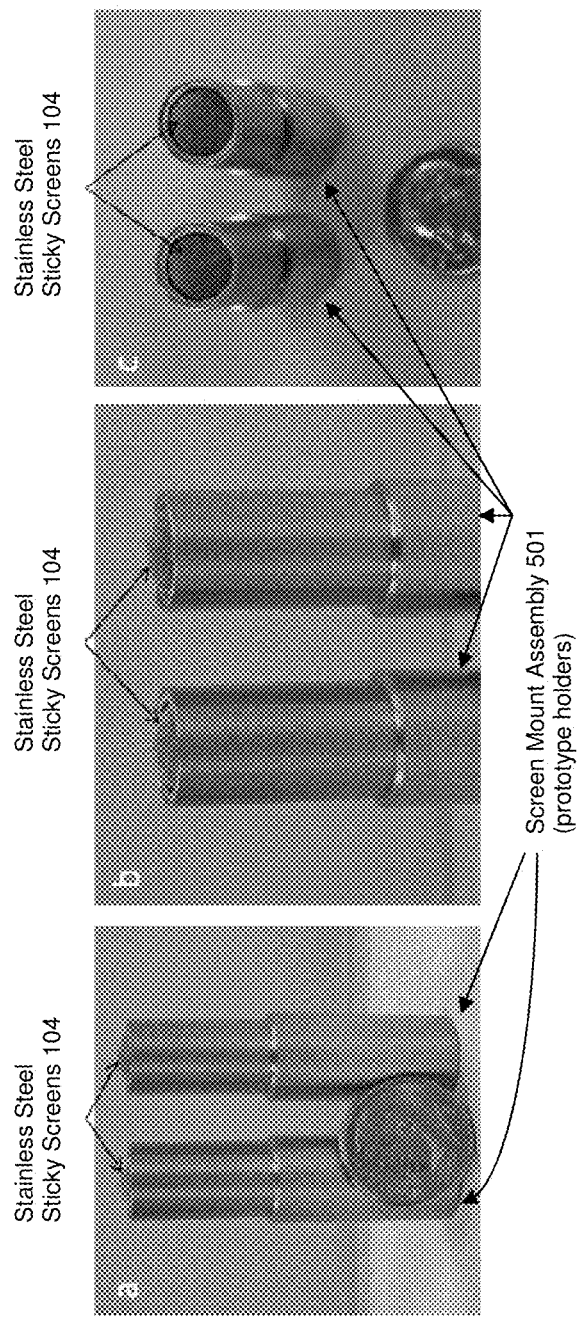
FIG. 2A illustrates a side view of an entire sample screen mount assembly (hereafter "screen mount assembly 501" prototype holder with stainless steel sticky screen(s) 104.
FIG. 2B illustrates a close up side view of the entire screen mount assembly 501 prototype holders, (b) with stainless steel sticky screen(s) 104 in screen mount assembly 501 prototype holders showing a domed shape of stainless steel sticky screen(s) 104, and (c) top view of screen mount assembly 501 prototype holders and stainless steel sticky screen(s) 104.
FIG. 2C illustrates a top view (c) of stainless steel sticky screen(s) 104 in screen mount assembly 501 prototype holders.

Referring to FIG. 1, the operational concept 101 of the sampler for a broad range of chemicals 301 (herein, also referred to as "SBRC 301") consists of an internal space 114 which is isolated from the sampling environment 102 (ambient environment) such that chemical aerosols and vapors cannot penetrate into the internal space 114 of the SBRC 301, effectively isolating any sample collection media contained within the SBRC 301. The sampling media (i.e., the sample screen(s)) can consist of any material that can capture aerosols, or vapors, or particulates on surfaces. Furthermore, the sample collection media can be made from glass, ceramic, fiberglass or other suitable material. In FIG. 1, a stainless steel screen coated with a sticky substance, such as stainless steel sticky screen 104, can capture all states of chemicals, aerosols, liquids, particulates on surfaces, and vapors. The stainless steel sticky screen 104 is described in FIG. 2A, FIG. 2B and FIG. 2C. FIG. 2A shows an example of (prototype holders) screen mount assembly 501 for the stainless steel sticky screen 104 held in the prototype holders. The stainless steel sticky screen 104 is designed to extend beyond the screen mount assembly 501 face, as shown in FIG. 2B, to enable the collection of particulates and/or liquid droplets on surfaces by pressing the stainless steel sticky screen 104 against the surface without contacting the screen mount assembly 501 body. Other types of screens, such as polymeric screens, can also be used instead of or in conjunction with the stainless steel sticky screen 104.

Referring to FIG. 1, FIG. 2A, FIG. 2B, FIG. 2C, and FIG. 5, exemplary embodiments of the sticky substance used for coating on the stainless steel sticky screen 104 includes partially polymerized polydimethyl siloxane (PDMS), however, any sticky coating or material can be used for low vapor chemical particulate collection.

Figures 7A, 7B:
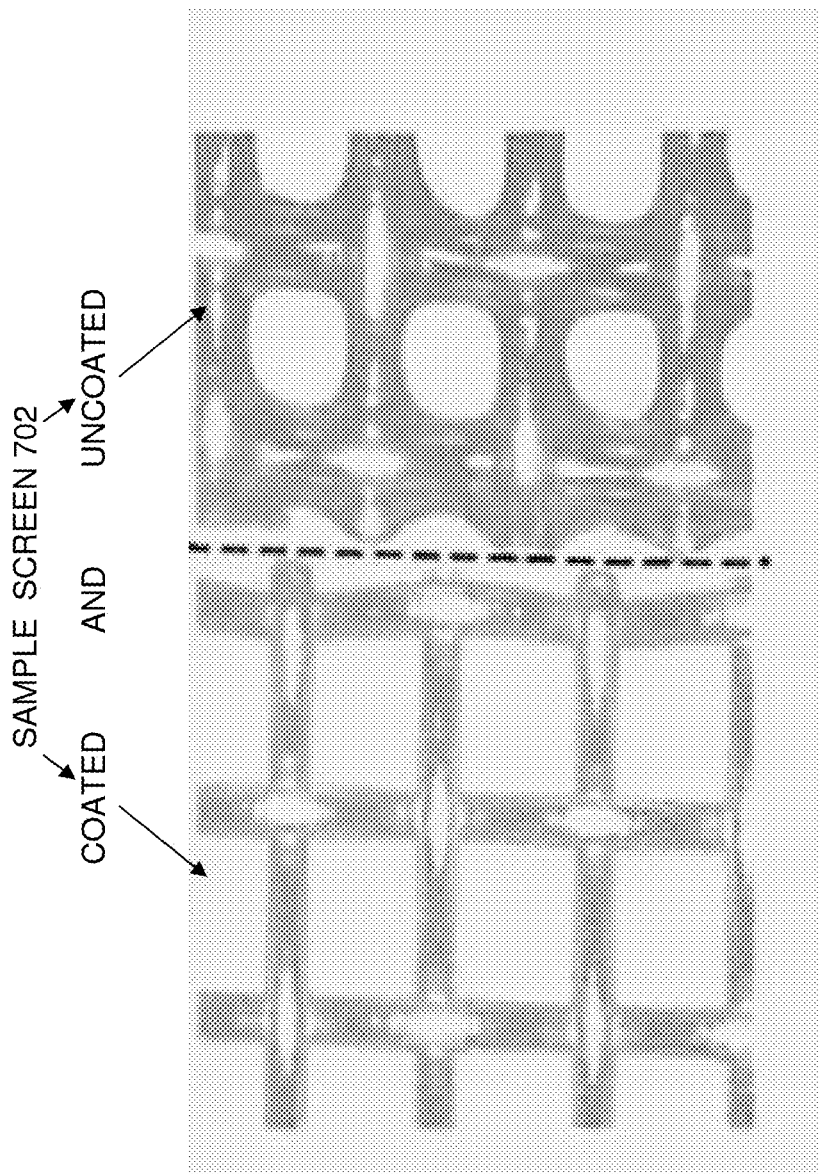
FIG. 7A illustrates a sample screen 702, which is not coated with any sticky substance.
FIG. 7B illustrates a sample screen 702, which is coated with a sticky substance; in this case the sticky substance is polymerized polydimethyl siloxane (PDMS).

FIG. 7A is a sample screen micrograph illustrating an uncoated sample screen 701, and FIG. 7B is a sample screen micrograph illustrating a coated sticky screen, such as stainless steel sticky screen 104.

Figure 3:
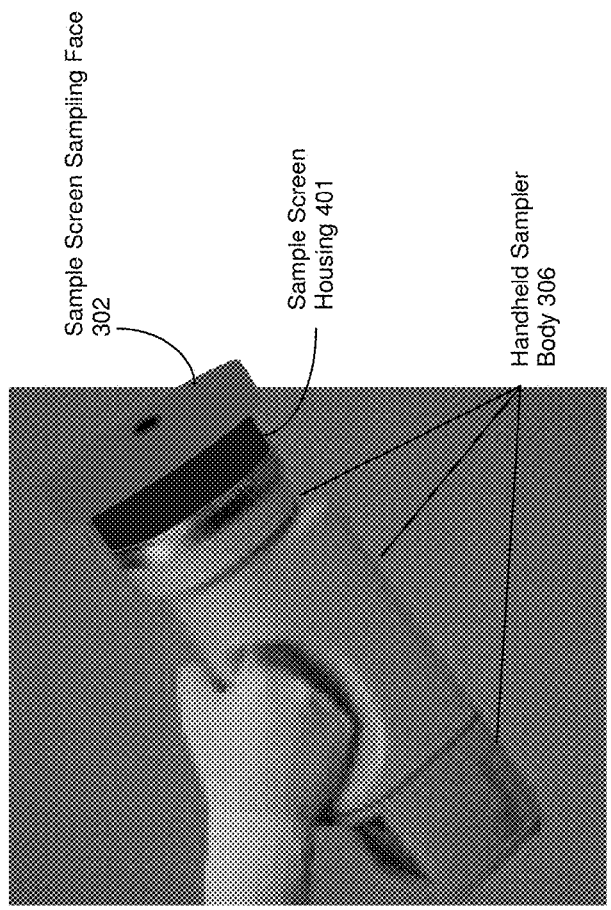
FIG. 3 illustrates the low vapor pressure toxic chemical sampler with handheld sampler body and sample screen housing. Sample screen(s) 702 are contained in the sample screen housing.

Referring to FIG. 1 and FIG. 3, the SBRC 301 is designed to expose the sampling media (in this case, the sampling media can be the sample screen 702) to the environment for sampling by physically pushing the sampling media/sample screen 702 out of the SBRC 301 sealed internal space 114 into the sampling environment 102 using a sampling cassette 106 associated with a retractable and expandable screen mount assembly 501, incorporating a draw tube 108, which both exposes the sampling media to the sampling environment 102 and enables air to be drawn through the sampling media through the draw tube 108. The unique feature of this approach is the placement of the sampling media to collect particulates and/or liquid droplets on surfaces (by pressing the sampling media onto the surface(s)) as well as collection of aerosols and chemical vapors by drawing air through the sampling media. Once the collection is completed the sampling media is drawn back inside, (retracted 116 from), the SBRC 301 and isolated from the sampling environment 102 to insure that the sampling media is not contaminated by the external sampling environment 102 or analyte is not lost prior to analysis.

It is important to emphasize that, the SBRC 301 system exemplary embodiments are capable of collecting chemical aerosols, chemical particulates and/or liquid droplets on operational surfaces, and chemical vapors using a single sampling device and format for collection and analysis of chemical contaminants. Furthermore, the collected Low Vapor Pressure Chemicals (LVPCs) can be analyzed using a number of different analytical techniques and instruments, including thermal desorption mass spectrometry, atmospheric ionization mass spectrometry, which includes atmospheric ionization techniques, i.e., Direct Analysis in Real Time (DART), Desorption Electrospray Ionization (DESI), as well as any other atmospheric ionization technique for mass spectral analysis. Also, the LVPCs can be analyzed on the sticky screen using Raman spectroscopy and IR spectroscopy.

In a first exemplary embodiment of the invention, the sample screen(s) include fine mesh stainless steel screens, such as stainless steel sticky screen 104, coated with a sticky substance, such as PDMS; thus, the stainless steel sticky screen(s) 104 (coated) are the capture media for aerosols, liquid droplets, particulates on surfaces, and chemical vapors. Collection of aerosols and chemical vapors is accomplished by drawing air through the stainless steel sticky screen(s) 104 media capturing aerosols and chemical vapors on the sticky surface of the stainless steel sticky screen(s) 104 for later analysis. For collection of particulates and/or liquid droplets on environmental surfaces, the stainless steel sticky screen 104 is physically pressed against the contaminated surface and any particulates and/or droplets on the surface are captured by the adhesive surface of the stainless steel sticky screen(s) 104.

Figure 6:
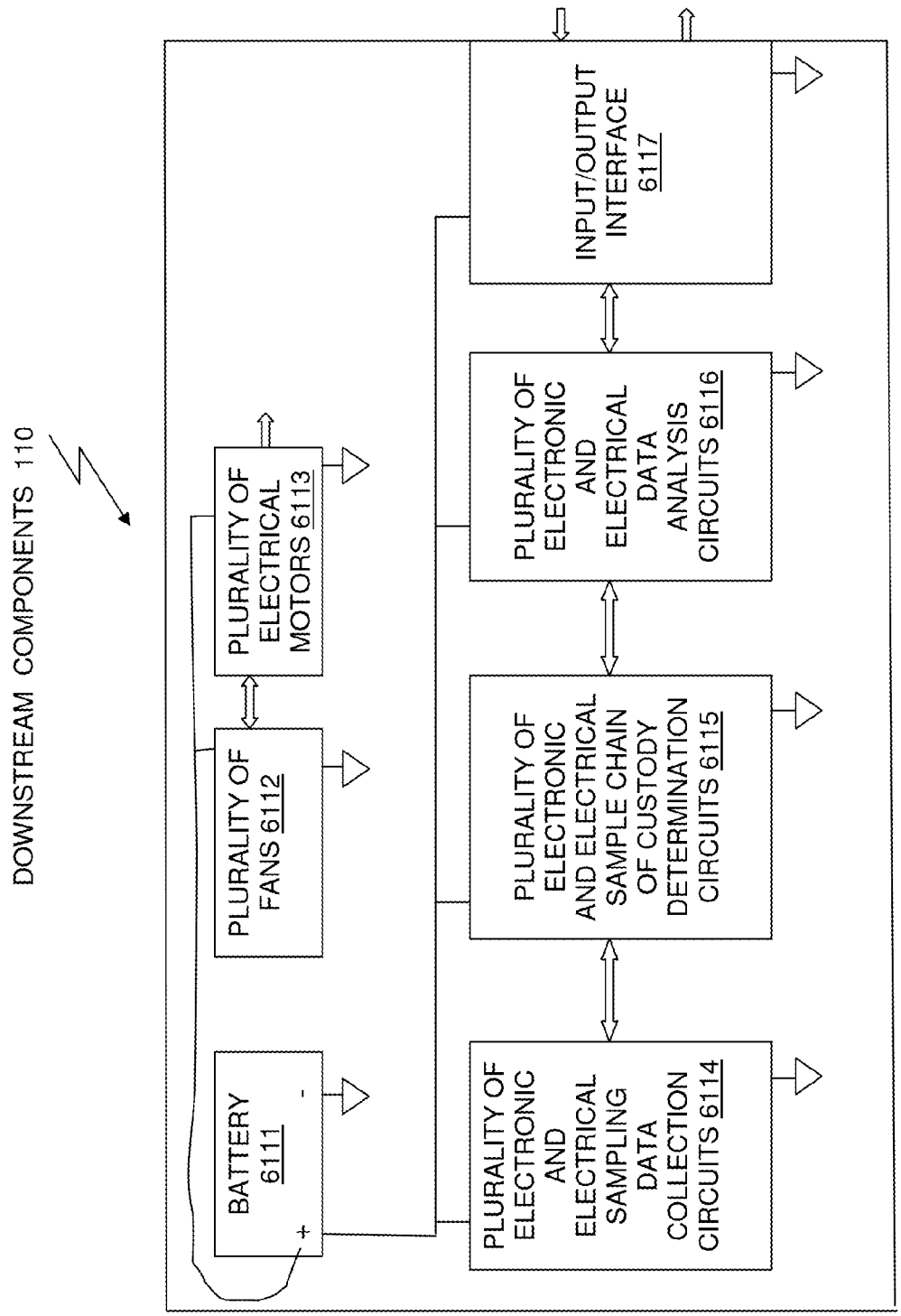
FIG. 6 illustrates downstream components 110.

Referring to FIG. 1 and FIG. 3, in a second exemplary embodiment illustrated in FIG. 3, the SBRC 301 consists of a handheld sampler body 306, sample screen housing 401, and sample screen sampling face 302. The handheld sampler body 306 operates electronic and electrical circuits from battery 6111 power, which enables the control of a volume of air sampled, and collects sampling data using electronic and electrical sampling data collection circuits 6114 and electronic and electrical sample chain of custody determination circuits 6115 and electronic and electrical data analysis circuits 6116 and input/output interface circuits 6117 to enable and/or cause sample chain of custody determination(s) after sample collection and during analysis of the sample. The handheld sampler body 306 also contains air draw 112 fans 6112 and motors 6113—which can be battery 6111 powered—(for air draw and/or vacuum) to cause air to flow through stainless steel sticky screen(s) 104. The sample screen housing 401 and the sample screen sampling face 302 contain the sample collection media and are designed to operate with any commercial off-the-shelf handheld sampler body 306. The sample collection media can be any medium or process which collects and/or captures chemical aerosols, particulates and/or liquid droplets on surfaces, as well as chemical vapors and aerosols. The sample screen housing 401 is designed to (1) isolate clean sampling media from the sampling environment 102; (2) expose a single sampling media to the sampling environment 102 for aerosol, chemical vapor, and/or particulate and/or liquid droplets on surface sampling; (3) isolate exposed sampling media from the sampling environment 102 and other exposed sampling media; and (4) interface via input/output interface 6117 with one or more of an analytical platform or a plurality of analytical platforms for rapid analysis of samples collected. The plurality of electrical motors 6113 part of the downstream components 110, can also mechanically and electrically interfaced (via input/output interface 6117) with the sampling cassette(s) 106 and other mechanical components housed in and/or connected to the handheld sampler body 306, of the Sampler of a Broad Range of Chemicals 301 apparatus/system (see FIG. 6). Further, in this second exemplary embodiment, the screen sampling media consists of a mesh, where the mesh is either metal or polymeric in nature, and thus forming a sample screen 702, such as a stainless steel sticky screen(s) 104 mesh, which can have an adhesive or sticky coating on the surface of the stainless steel sticky screen(s) 104 mesh. The coated screen, such as the stainless steel sticky screen(s) 104 retains the porous nature of the original screen sampling media enabling air to be drawn through the stainless steel sticky screen(s) 104 or plurality of stainless steel sticky screens 104 by the handheld sampler body 306. The screen mesh can vary from a mesh size 400 (i.e., 36 μm holes) to a mesh size 100 (i.e., 152 μm holes) or larger if necessary. The coating on the stainless steel sticky screen(s) 104 ranges from thin (10-20 μm) to thick (50-100 μm) depending on the flow rate and capture efficiency required. The stainless steel sticky screen(s) 104 can be used singly or layered in stacks to increase the collection efficiency. To enable the collection of particulates and/or droplets on surfaces, the sample screen 702 is mounted such that the sample screen 702 forms a surface that extends beyond the screen mount assembly 501, enabling surface sampling such that only the sample screen 702 contacts the surface being sampled.

Figure 4:
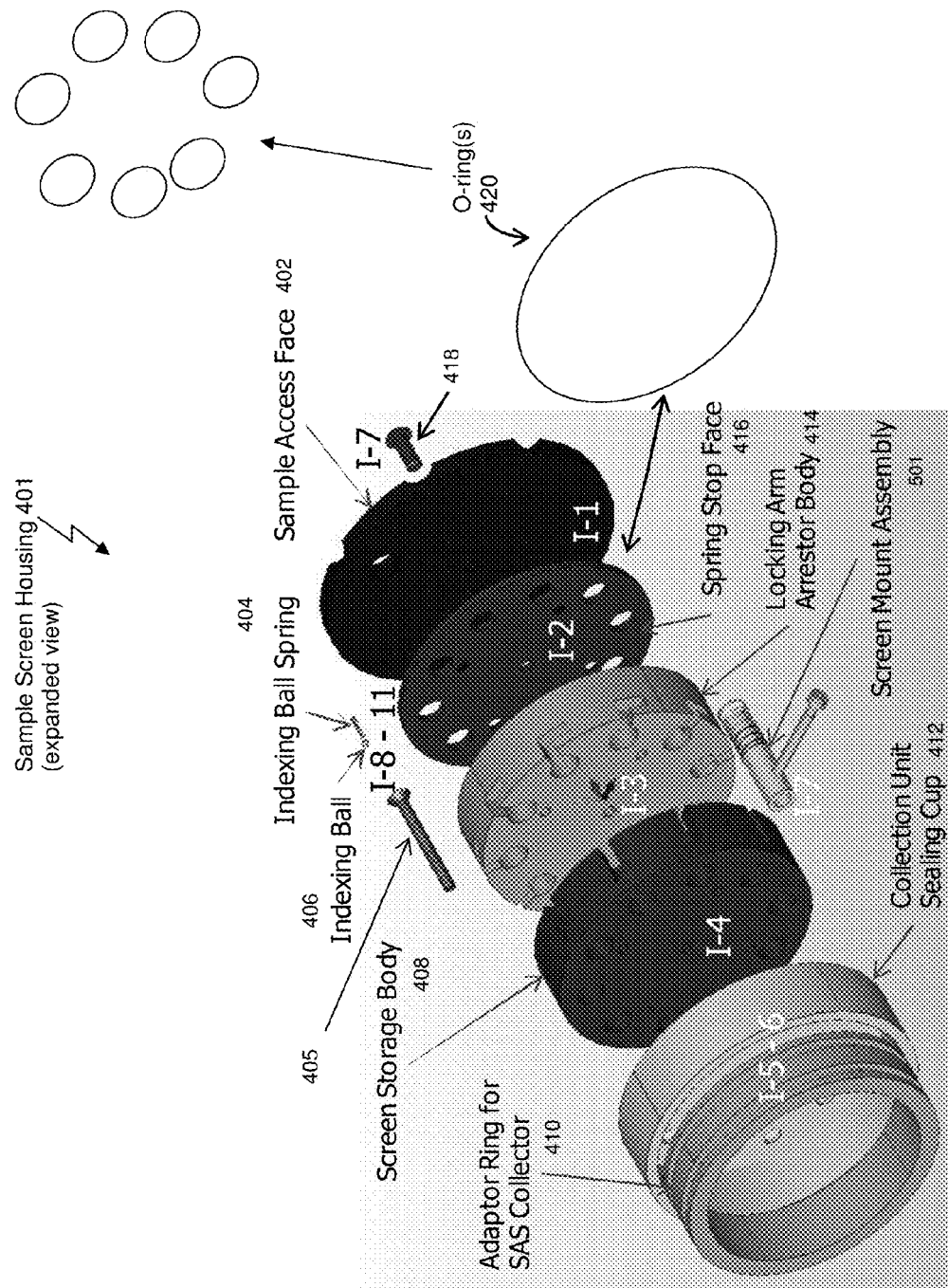
FIG. 4 illustrates an expanded view of the different components of the sample screen housing including the screen mount assembly.

FIG. 4 illustrates the expanded design for a third exemplary embodiment of the sample screen housing 401 consisting of nine major components:

(1) Sample Access Face 402;
(2) Indexing Ball Spring 404;
(3) Indexing Ball 406;
(4) Spring Stop Face 416;
(5) Locking Arm Arrestor Body 414;
(6) Screen Mount Assembly 501;
(7) Screen Storage Body 408;
(8) Collection Unit Sealing Cup 412; and
(9) Adaptor Ring for Commercial off-the-Shelf SAS Collector 410.

Figure 5:
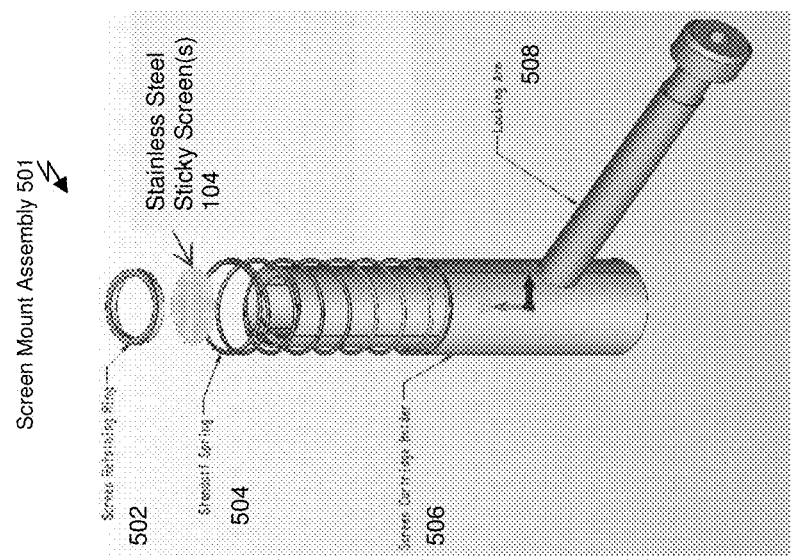
FIG. 5 illustrates a sample screen mount assembly for holding one sticky screen.

In the third exemplary embodiment the screen storage body 408 contains a plurality of screen mount assembly 501 units, each holding one stainless steel sticky screen 104. The design of the screen mount assembly 501 is illustrated in FIG. 5, where the stainless steel sticky screen 104 is mounted in said screen mount assembly 501. The advantage of this design is that the screen mount assembly 501 can be reused after sampling and analysis simply by removing the old sample screen 104 and retaining ring 502. The stainless steel sticky screen 104 is designed to extend beyond the body of the screen mount assembly 501, so that various surfaces can be directly sampled by pressing or swiping the stainless steel sticky screen(s) 104 against a surface. Furthermore, in the third exemplary embodiment, the stainless steel sticky screen(s) 104 is in a dome shape as shown in the illustration of FIG. 2B; however, other screen shapes can be used, including a "top hat" shape (such as Top Hat screen 1502) where the top of the screen is flat; other screen shapes can also be employed to vary the angle of the screen surface with respect to the sample air flow in order to increase aerosol collection efficiency.

Figure 10A:
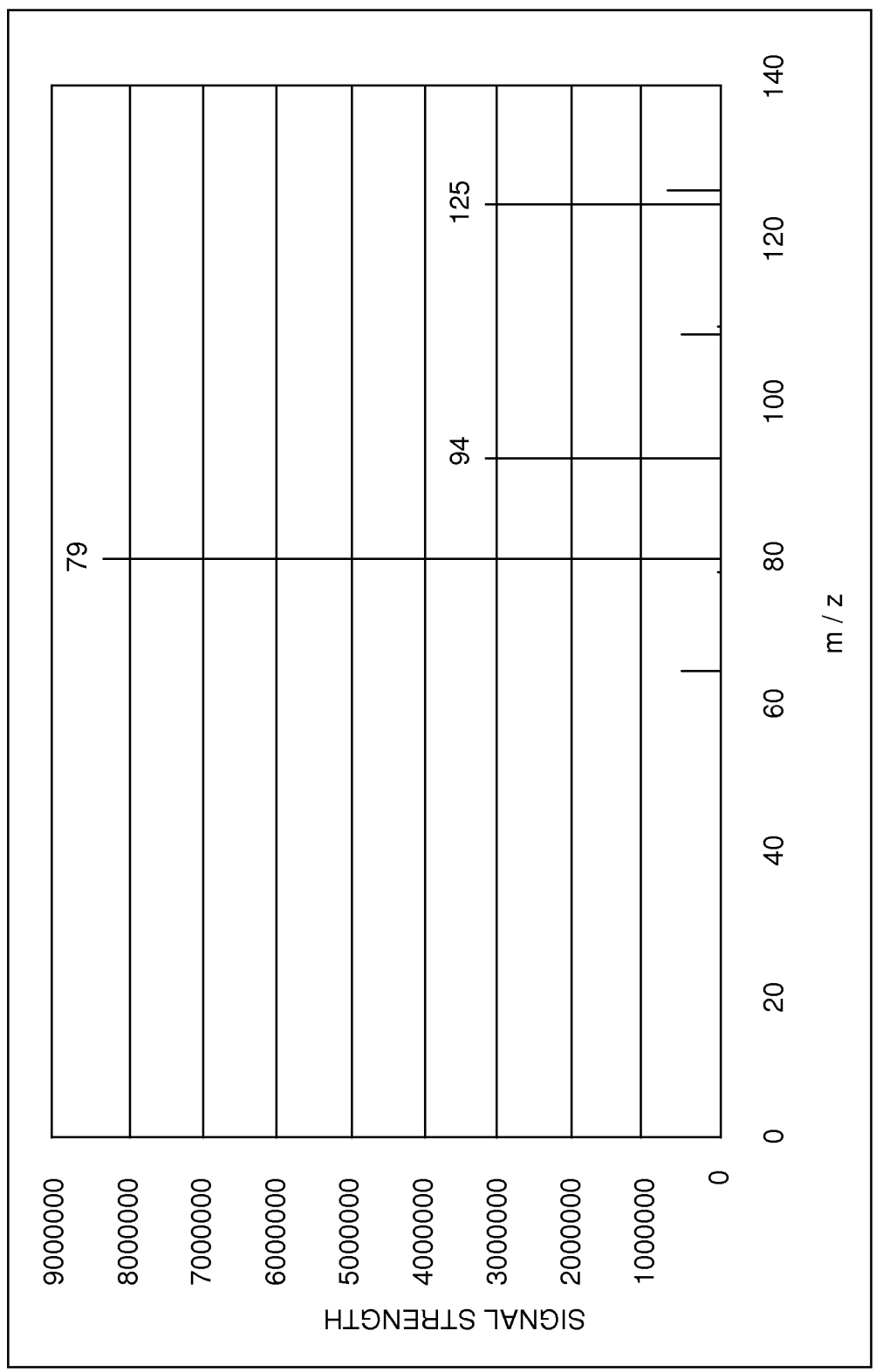
FIG. 10A illustrates a mass spectrum graphic of DMMP/SG collected onto a stainless steel sticky screen 104, coated with PDMS.
Figure 10B:
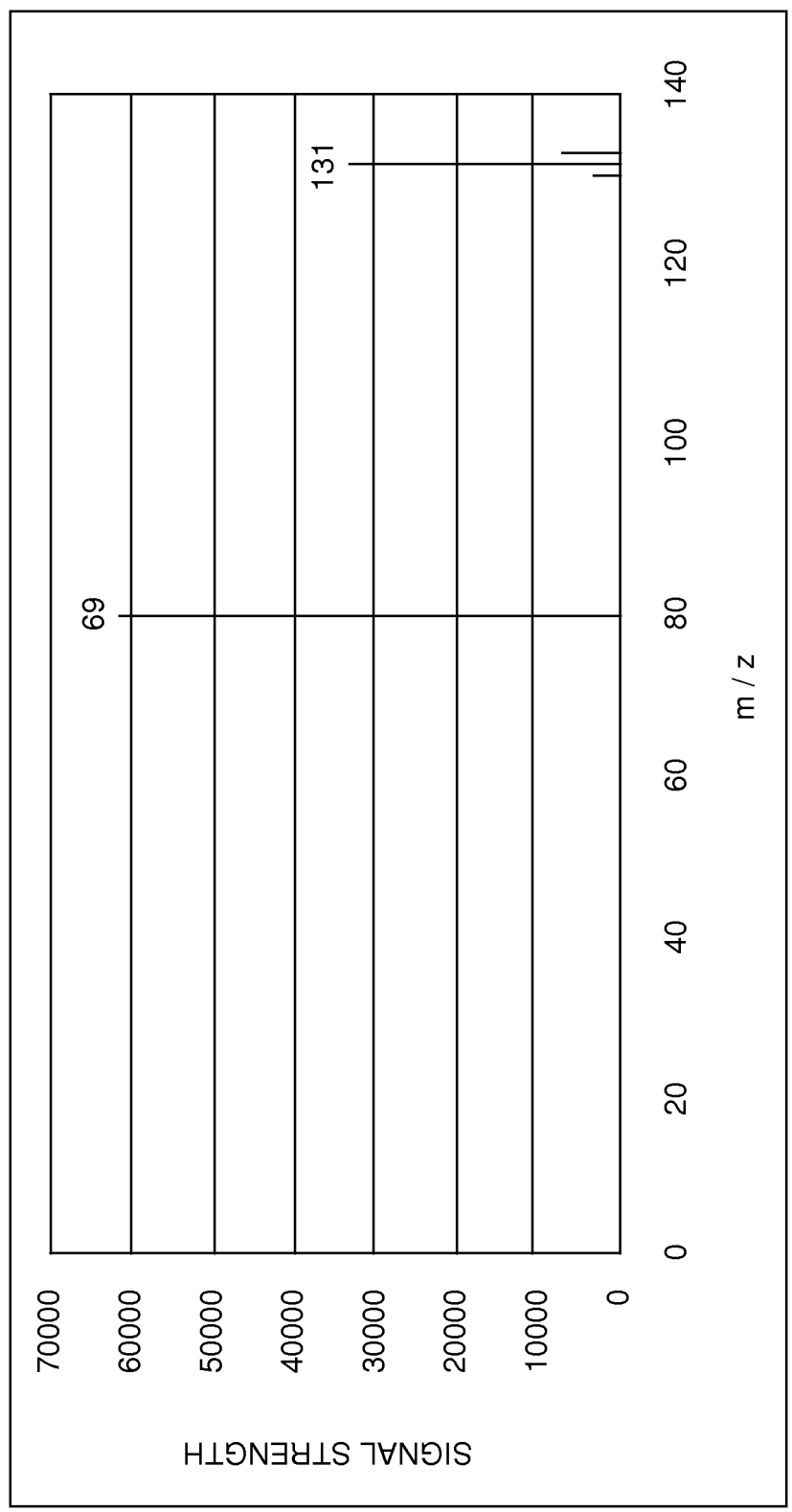
FIG. 10B illustrates a mass spectrum graphic of a blank sample screen 702 coated with sticky PDMS, but not coated with captured particulates.

Referring to FIG. 1, FIG. 4 and FIG. 5, sample collection is initiated by first rotating the sample access face 402 of the sample screen housing 401, such that a sampling port in the sample access face 402 aligns with the cylinder formed by the locking arm arrestor body 414 and screen storage body 408 unit which contains a single screen mount assembly 501, where a long screw 405 extends through the locking arm arrestor body 414 into the screen storage body 408. The sample access face 402 is indexed such that the sampling port, in the front face of the sample access face 402, will align with a cylinder in the locking arm arrestor body 414 and screen storage body 408 unit, containing a single screen mount assembly 501 or the blank face of the screen storage body 408. To begin a sampling operation, an operator pushes up the locking arm 508 to extend the sampling screen outside of the sample screen housing 401 body. The locking arm 508 is pushed clockwise (as seen from the rear of the handheld sampler body 306) thus, placing the locking arm 508 into the locked position in the locking arm arrestor body 414. In this position the screen retaining spring 502 is fully compressed in the screen mount assembly 501 and the screen mount assembly 501 containing the stainless steel sticky screen 104 is extended into the sampling environment 102. Once in this position, the sampler for broad range of chemicals 301 is ready to collect either aerosol samples or particulate and/or liquid samples from various surfaces in the sampling environment 102. One important feature illustrated in FIG. 4 is that one or more o-ring(s) 420 of a plurality of o-rings 420 are mounted on the spring stop face 416 which (1) seal around the screen mount assembly 501 during sampling and (2) seal against the sample access face 402 prior to and after sampling thereby protecting the sampling screen from environmental contamination from the sampling environment 102. After collecting a sample, the locking arm 508 is pushed counter-clockwise (as seen from the rear of the handheld sampler body 306) causing the standoff spring 504 to retract 116 the screen mount assembly 501 into the screen storage body 408. After retracting 116 the screen mount assembly 501 into the screen storage body 408, the sample access face 402 is turned counter clock-wise (as seen from the rear of the handheld sampler body 306) to the next indexed site which corresponds to the blank face of the locking arm arrestor body 414. When in this position, all screens are effectively isolated from the sampling environment 102 and each other. To start a second sampling run, the sample access face 402 is turned counter clock-wise to the next indexed site which exposes a fresh screen mount assembly 501 and sampling screen, where a short screw 418 extends through the sample access face 402 into the spring stop face 416. The system is designed such that the sample access face 402 can only be turned in one direction, thereby eliminating the possibility of exposure of an already exposed sampling screen.

Referring to FIG. 1 and FIG. 3, the handheld sampler for a broad range of chemicals 301 disclosed herein has a number of significant advantages over commercially available sampling devices. Any given commercially available collector cannot collect all physical forms of target analyte; vapors, aerosols, or particulates on surfaces. However, the handheld sampler for a broad range of chemicals 301 herein disclosed enables the collection of aerosolized materials (solid particulates and liquid droplets), solid particulates/liquid droplets on surfaces by exposing a specialized surface designed to collect all three forms of analytes. In exemplary embodiments, the handheld sampler for a broad range of chemicals 301 is designed to utilize metal mesh screens, such as stainless steel sticky screen(s) 104 which are coated with a sticky substance which can capture aerosols, and vapors in the air and particulates and droplets on surfaces. The handheld sampler for a broad range of chemicals 301 is designed to use these sampling methods and protocols, to collect all of the targeted samples in the air and on surfaces and to protect the sampling media from exposure to the sampling environment 102 both prior to and after sampling through using a particular medium.

FIG. 8A illustrates a stainless steel sticky screen 104 prior to sampling. FIG. 8B illustrates a stainless steel sticky screen 104 having chemical particulates collected by the stainless steel sticky screen 104, after surface contact with a surface contaminated with dimethyl methylphosphonate immobilized into a silica gel matrix (DMMP/SG).

Referring again to FIG. 6, downstream components 110, including data collection circuits 6114, sample chain of custody circuits 6115, data analysis circuits 6116 and including input/output interface 6117 elements, all of which provide access to a plurality of analytical platforms for rapid analysis of samples collected, where the plurality of analytical platforms for analysis include the use of desorption-ion trap mass spectrometry (TD-CIMS). FIG. 9A and FIG. 9B illustrate the TD-CIMS, which consists of a Direct Analysis in Real Time (DART) ambient ionization system and a cylindrical ion trap mass spectrometer (DART-CIMS).

In an exemplary embodiment, analysis of the particulates collected on the stainless steel sticky screen(s) 104 can be accomplished by placing the stainless steel sticky screen(s) between the DART outlet and the mass spectrometer inlet as shown in FIG. 9B, where hot gas from the DART system impacts the particulates on the sticky screen where the DMMP contained in the silica gel particulates is volatilized and carried into the mass spectrometer inlet. The mass spectrum of a stainless steel sticky screen 104 contaminated with DMMP/SG particulates and a blank stainless steel sticky screen 104 (i.e., no particulate sampled) are illustrated in FIG. 10A and FIG. 10B respectively. The peaks due to DMMP at m/z 79 and m/z 125 are observed in FIG. 10A for the analysis of the DMP/SG, while they are absent in analysis of the stainless steel sticky screen 104 blank shown in FIG. 10B.

Figure 11:
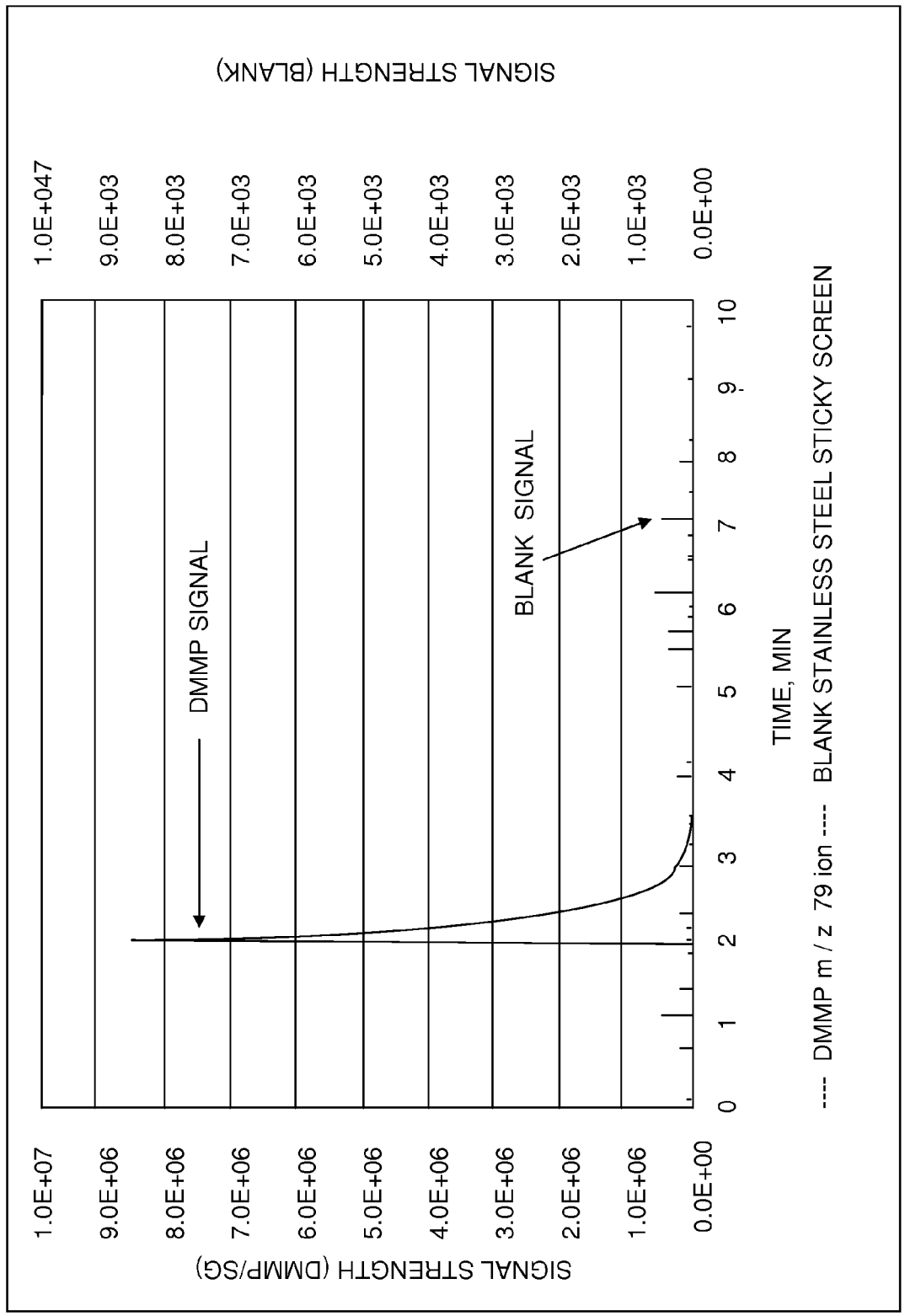
FIG. 11 illustrates a plot of signal strength versus time of DMMP ions.

The response of the mass spectrometer to the DMMP m/z 79 ion versus time is plotted with respect to time in FIG. 11, where the signal strength for the m/z 79 ion increases rapidly 6 seconds after the introduction of the sample into the hot nitrogen DART stream and decays to background after 5 minutes in the hot nitrogen DART stream. The area under this curve enables the calculation of the detection limit for the DMMP/SG particulate, where DMMP/SG Detection Limit=0.97 nanograms.

Figure 15:
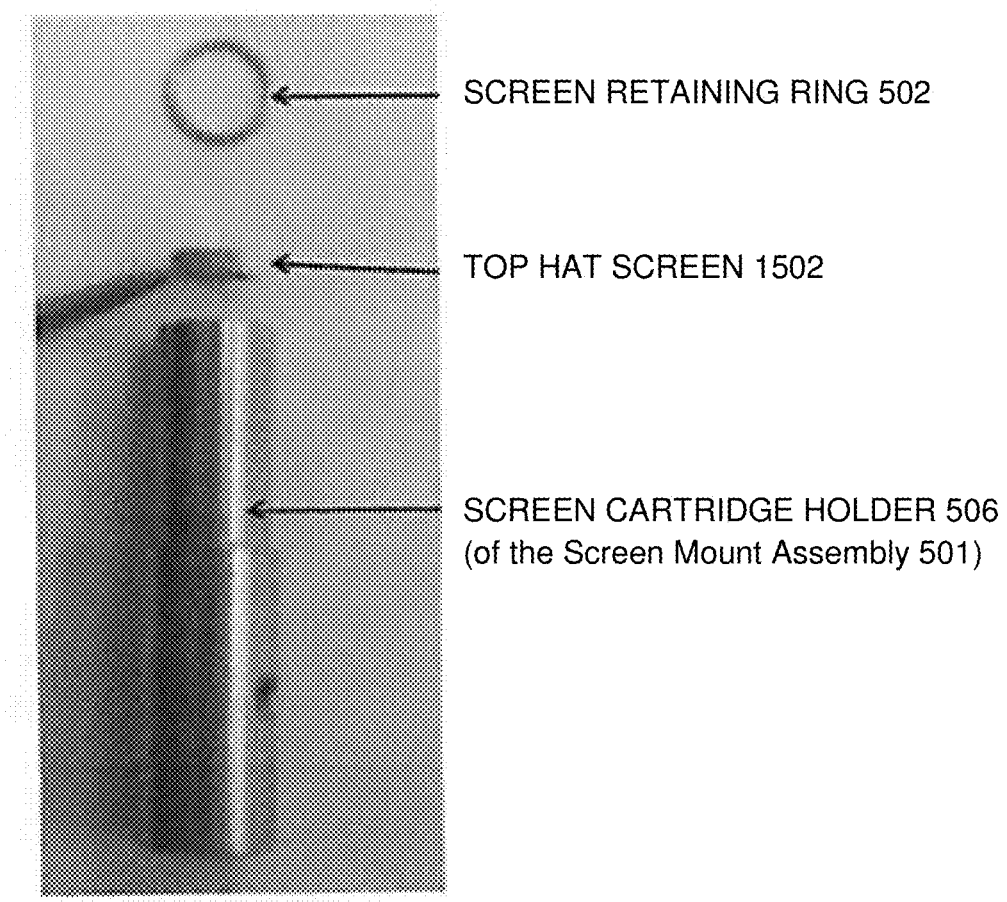
FIG. 15 illustrates a Top Hat screen 1502 (which is flat) along with a screen retaining ring 502 and a screen cartridge holder 506.

In another exemplary embodiment, stainless steel sticky screen(s) 104 having the mesh of about 150 μm holes were assembled into a top hat (FIG. 15) configuration with an 8 mm diameter flat sampling/analysis area. The screen mount assembly holder 501 holds the stainless sticky screen 104 for both sampling and analysis. In FIG. 15, an uncoated Top Hat screen 1502 is placed onto a recessed ledge in the end of the screen cartridge holder 506. A screen retaining ring 502 is press fitted into the screen cartridge holder 506, such that the Top Hat sample screen 1502 is held in place. The mounted Top Hat screen 1502 is then spray coated with partially polymerized PDMS. This treatment results in a sticky PDMS coating on the screen capable of capturing particulates either through direct surface contact or by impaction of the particulates on the stainless steel sticky screen 104. An additional advantage of this sampler is that after sampling and analysis, the used stainless steel sticky screen(s) 104 and the screen retaining ring 502 can be removed and a new sample screen placed into the screen cartridge holder 506.

Figures 12A, 12B:
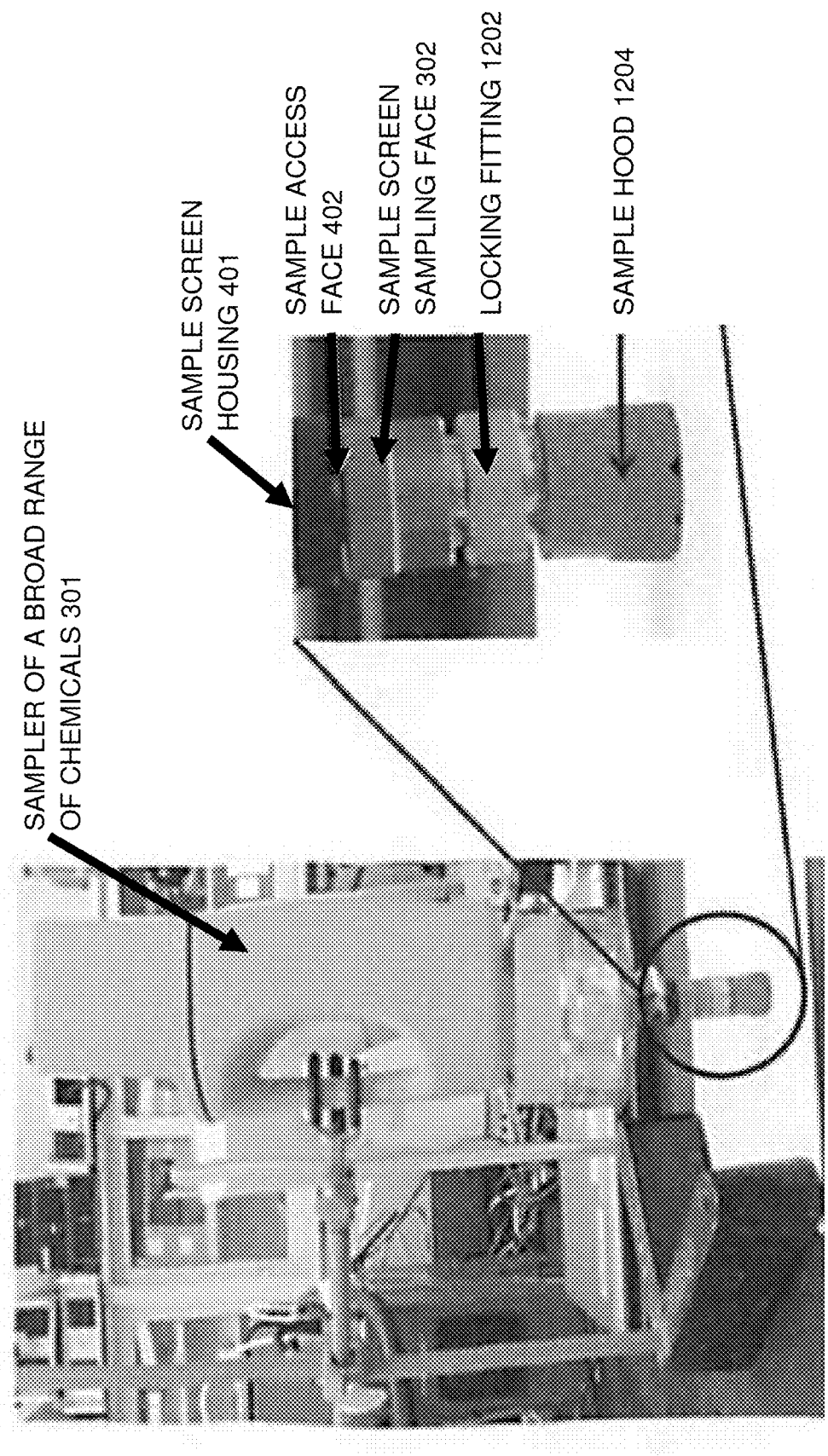
FIG. 12A illustrates the hand held Sampler of a Broad Range of Chemicals 301 configured and fitted with a sample screen housing 401, containing a stainless steel sticky screen 104 and positioned to collect aerosolized particulates from a surface, by way of a sample hood 1204 connected via a locking fitting 1202.
FIG. 12B illustrates the sample screen; housing 401 the sample screen sampling face 302 configured with the locking fitting 1202 and the sample hood 1204.

FIG. 12A and FIG. 12B illustrate an exemplary embodiment accomplishing collection of particulates from a contaminated surface by aerosolizing particulates on the surface. In this exemplary embodiment, a commercial bioaerosol collector is used as the vacuum source to pull particulate laden air through the stainless steel sticky screen(s) 104. A sampling hood 1204 with air vents cut into the sides is configured to fit onto the end of a locking fitting 1202, such as SWAGELOK, connected to the screen mount assembly 501, via the sample screen sampling face 302. The sampling hood 1204 generates a turbulent air flow over the surface being sampled. Upon activation of the bioaerosol collector blower, air is drawn through the vents in the sampling hood 1204 and over the surface effectively sweeping particulates up into the air flow. Once in the air flow, the particulates impact the stainless steel sticky screen 104 and are captured for analysis.

After sample collection of particulates, the screen mount assembly 501 is removed from the sampler of a Broad Range of Chemicals 301 device and placed into an analytical system, as illustrated in FIG. 9A and FIG. 9B, where FIG. 9A illustrates a configuration of the entire DART-CITMS system in conjunction with the screen mount assembly 501 (containing the stainless steel sticky screen(s) 104) placed into the analytical system, in which the DMMP in the silica gel is thermally desorbed (i.e., generating gas phase ions) using a Direct Analysis in Real Time atmospheric ionization system; thus, the DMMP/SG is desorbed into a Cylindrical Ion Trap Mass Spectrometer (CITMS). And, FIG. 5 illustrates a close up view of the screen mount assembly 501 (containing the stainless steel sticky screen 104) situated between the DART outlet and the CITMS inlet.

In exemplary embodiments, the Direct Analysis In Real Time atmospheric ionization system is operated in the positive ion mode; gas temperature is set at 250 degrees centigrade min (250° C.) with a flow rate of 1 Liter mm$^{-1}$; however, different temperatures and gas flow rates can be used for different analytes.

Figure 13B:
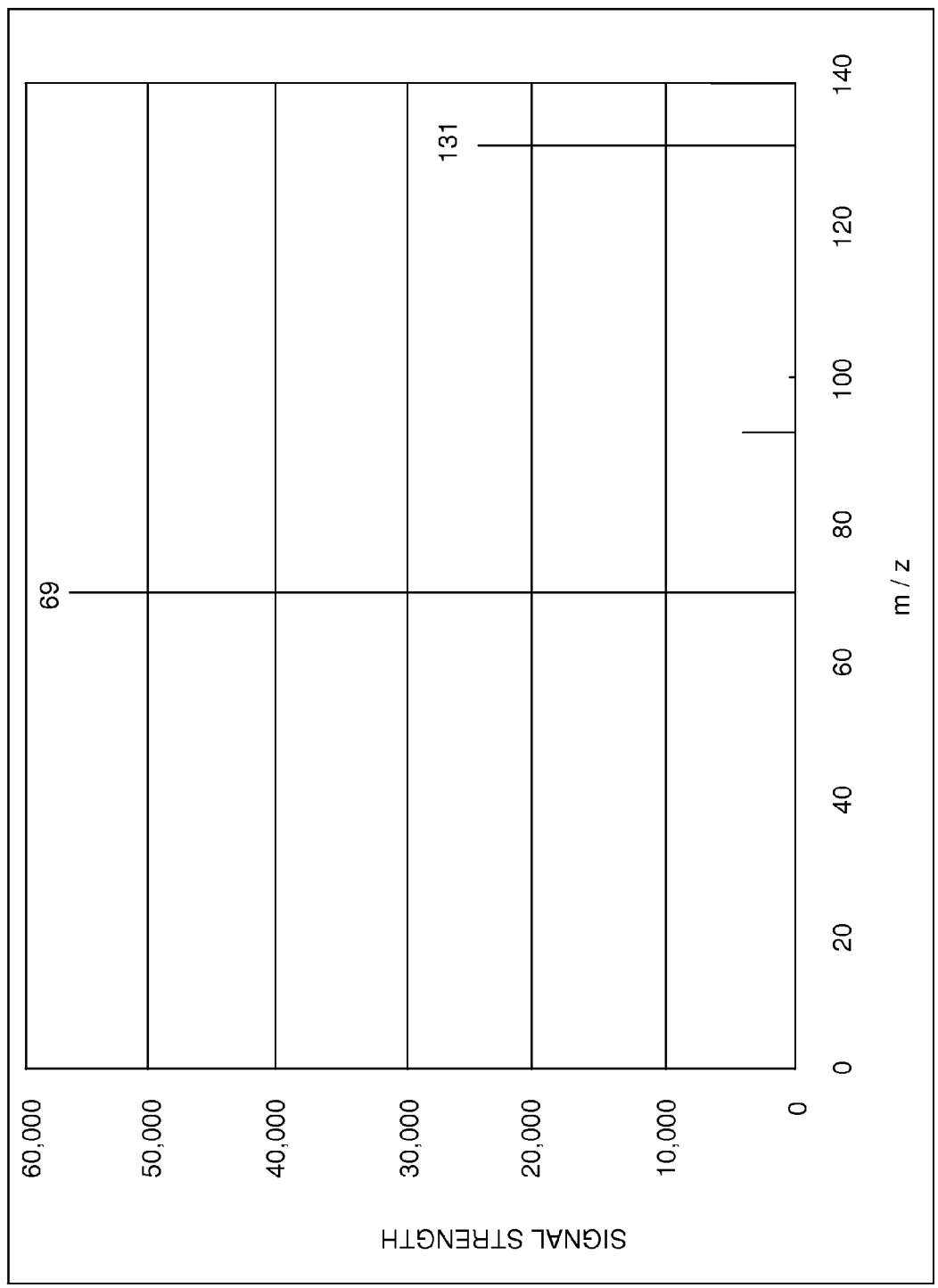
FIG. 13B illustrates a mass spectrum graphic of a blank sticky screen.

A graphic of the mass spectrum of a sample of the DMMP/SG particulates and a graphic of the mass spectrum of a blank stainless steel sticky screen 104 sample screen are illustrated in FIG. 13A and FIG. 13B respectively.

The mass spectrum of the DMMP/SG particulates illustrated in FIG. 13A exhibits a single intense peak for DMMP at m/z 79; the parent ion peak at m/z 124 is observed; however, significantly less intense than the m/z 79 DMMP peak.

The mass spectrum of the blank stainless steel sticky screen 104 illustrated in FIG. 13B shows two peaks at m/z 69 and m/z 131, which are due to the internal standard perfluorotributylamine used in the FLIR CHEMSENSE 600 ITMS; there is no indication of the characteristic DMMP peaks in the blank mass spectrum; and The detection limits for DMMP/SG particulate with different DMMP loadings are presented in Table 1, based on the calculated DMMP detection limit of 87 micrograms. As expected, the detection limit for DMMP/SG particulates decreases as the loading of DMMP increases form 3.0% (wt) to 26.7% (wt) in the silica gel particulates.

TABLE 1

| DMMP Concentration, Wt % | Particulate DL, mg |
| --- | --- |
| 3.0 | 2.9 |
| 13.0 | 0.67 |
| 26.7 | 0.33 |

Thus, Table 1 represents calculated detection limits for DMMP/SG particulates containing differences in weight percent of DMMP.

Because the sample screens are rigid, their shape and profile are highly repeatable enabling highly reproducible positioning into an analytical system. This results in highly reproducible signals for collected chemical particulates which enable very low detection limits for chemical particulates. Also, the stainless steel sticky screen(s) 104 surface shape can be tailored to be flat or curved or have a plurality of surface configurations, see FIG. 2A and FIG. 5.

Figure 14:
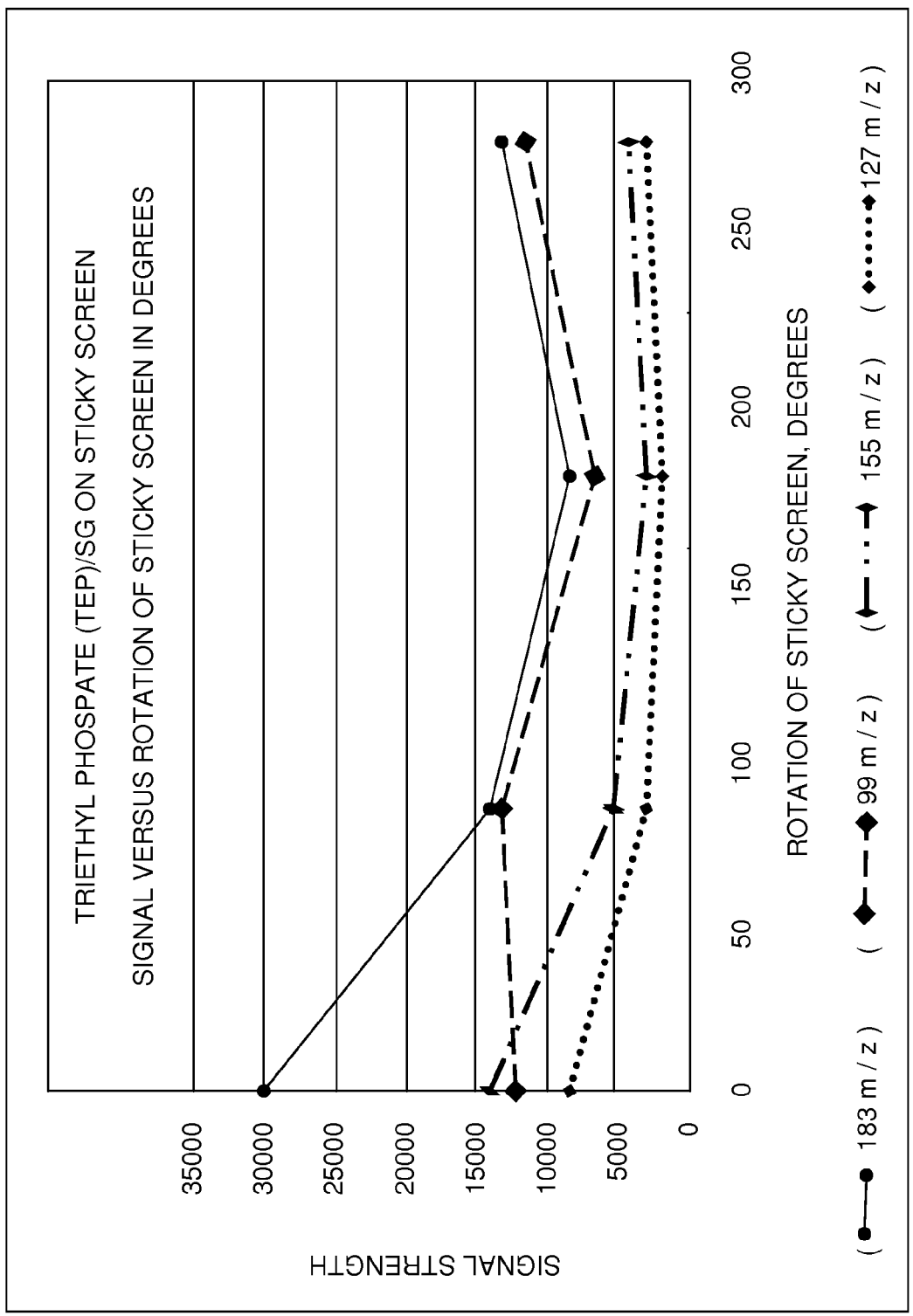
FIG. 14 illustrates a graph of signal strength versus rotational angle of a sticky screen.

The size of the holes in the stainless steel sticky screen(s) 104 can be controlled ranging from about 100 nanometers, for capture of extremely fine particulates, to hundreds of microns, depending on the size and type of particulate being targeted. It is understood that both the shape of the stainless steel sticky screen(s) 104 and the size of the holes can be tailored for improved collection and transfer to the detection system. An additional advantage of the sampler of broad range of chemicals 301 device is that multiple analyses can be performed for the same or different analytes. One approach to obtaining multiple analyses is to rotate the sampler of broad range of chemicals 301 device which causes the vaporization and ionization of the target analyte in one specific region of the stainless steel sticky screen(s) 104; thus, in this manner, multiple analyses can be obtained in light of signal strength versus rotational angle of the stainless steel sticky screen(s) 104 position, as illustrated in FIG. 14.

While the exemplary embodiments have been particularly shown and described with reference to preferred embodiments thereof, it will be understood, by those skilled in the art that the preferred embodiments including the first exemplary embodiment, and the second exemplary embodiment and the third exemplary embodiment have been presented by way of example only, and not limitation; furthermore, various changes in form and details can be made therein without departing from the spirit and scope of the invention. Thus, the breadth and scope of the present exemplary embodiments should not be limited by any of the above described preferred exemplary embodiments, but should be defined only in accordance with the following claim and/or claims and their equivalents. Any and/or all references cited herein are each entirely incorporated by reference herein, including all data, tables, figures, and text presented in the cited references. Also, it is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art. The foregoing description of the specific embodiments will so fully reveal the general nature of the invention that others can, by applying knowledge within the skill of the art, readily modify and/or adapt for various applications such specific embodiments, without undue experimentation, and without departing from the general concept of the exemplary embodiments. Therefore, such adaptations and modifications are intended to be within the meaning and range of equivalents of the disclosed embodiments, based on the teaching and guidance presented herein.

What is claimed is:

1. A sampler of a broad range of chemicals (SBRC) device, the SBRC device comprising:
    a handheld sampler body mechanically and communicatively coupled to
    a sample screen sampling face; and
    a sample screen housing,
        wherein, the sample screen housing further consists of:
        an adapter ring,
        a screen storage body,
        a spring stop face,
        an indexing ball,
        an indexing ball spring,
        a sample access face, having a short screw, and
        a locking arm arrestor body having a long screw,
            wherein, the locking arm arrestor body further consists of:
                a screen mount assembly including a draw tube,
                    wherein, the screen mount assembly further consists of:
                    a locking arm communicatively coupled to
                    a screen cartridge holder,
                    a standoff spring extendably and retractably coupled to the screen cartridge holder,
                    a screen, mounted on the standoff spring, and
                    a screen retaining ring mountably coupled to the screen and retaining the screen on the standoff spring, wherein the screen is retractably positioned between the spring stop face and the sample access face and positioned in the sample access face upon mechanical activation of the screen mount assembly in one of an extended position and a retracted position, wherein in the retracted position, the screen mount assembly causes the screen to be isolated from a sampling environment, wherein in the extended position, the screen mount assembly causes the screen to be engaged in and to be exposed to the sampling environment and to collect available samples of the broad range of chemicals in the extended position, wherein the draw tube causes air to be drawn through the screen further causing chemical contaminants and particulates, transferred via aerosols and chemical vapors, to be deposited on the screen.

2. The SBRC device of claim 1, wherein the handheld sampler body further comprises a battery, a plurality of fans, and a plurality of electrical motors, wherein the plurality of fans and the plurality of electrical motors are communicatively coupled to and powered by the battery, and wherein the plurality of fans and the plurality of electrical motors cause forced air draw through the screen, which causes the screen to collect available samples of the broad range of chemicals.

3. The SBRC device of claim 1, wherein the handheld sampler body further comprises a plurality of electronic and electrical sampling data collection circuits, and a plurality of electronic and electrical sample chain of custody determination circuits and a plurality of electronic and electrical data analysis interface circuits causing sample chain of custody determination after sample collection associated with sample analysis.

4. The SBRC device of claim 1, wherein the screen, mounted on the standoff spring extends beyond the sample access face, when the screen mount assembly is in the extended position and pressed against surfaces in the sampling environment, wherein the screen contains a coating of a sticky substance, causing the screen to have an adhesive surface, wherein collection of the broad range of chemicals includes collection of one or more of a plurality of particulates and of a plurality of liquid droplets when the screen is pressed against surfaces in the sampling environment, and wherein the plurality of particulates and the plurality of liquid droplets are adhered to the screen by the sticky substance coated on the screen.

5. The SBRC device of claim 4, wherein the screen comprises a mesh of holes ranging from about 36 μm holes up to about 152 μm holes, and wherein the sticky substance causing the screen to have an adhesive surface can be applied in coated thicknesses selected from a group of thicknesses in a range from about 10 μm thick up to about 20 mm thick and in a range of about 50 μm thick up to about 100 μm thick forming a fine mesh screen.

6. The SBRC device of claim 5, wherein the screen is selected from a group of screens consisting of a stainless steel sticky screen and a polymeric screen and a dome shaped screen and a flat shaped screen.

7. The SBRC device of claim 5, wherein the screen forming the fine mesh screen is a plurality of fine mesh screens stacked together.

8. A method of sampling a broad range of chemicals (SBRC) using an SBRC device having a handheld sampler body, a sample screen sampling face, a sample access face, a sample screen housing, a locking arm and a locking arm arrestor body including a screen mount assembly having a sampling screen mounted on the screen mount assembly, wherein the screen mount assembly further including a draw tube, a screen cartridge holder and a standoff spring extendably and retractably communicatively coupled to the locking arm, the method comprising:
    exposing the sampling screen to a sampling environment by a sampling method selected from a group of sampling methods consisting of at least one of:
        rotating the sample access face, aligning a sampling port in the sampling access face, wherein the sample access face can only be turned in one direction;
        extending the screen mount assembly through the sample screen housing and the sample screen sampling face:

manipulating the locking arm causing compression of the standoff spring, and positioning the locking arm in a locked position in the locking arm arrestor body, wherein the screen mount assembly includes the draw tube, wherein by positioning the locking arm in the locked position, causing the sampling screen to be positioned protruding beyond an outside surface of the sample screen face, and drawing through the draw tube, air from the sampling environment containing a plurality of airborne chemical contaminants causing the plurality of airborne chemical contaminants including aerosol particulates to be collected by and adhered to the sample screen; and extending the screen mount assembly through the sample screen housing and the sample screen sampling face: manipulating the locking arm causing compression of the standoff spring, positioning the locking arm in a locked position in the locking arm arrestor body, and pressing a first surface of the sample screen against a second surface of an object situated in the sampling environment, and collecting, onto the first surface, a plurality of solid particles and a plurality of liquid droplets containing a plurality of particulates from the second surface, wherein positioning the locking arm in the locked position, causes the sampling screen to be positioned protruding beyond an outside surface of the sample screen face; and removing the sampling screen from the sampling environment and isolating the plurality of airborne chemical contaminants, the plurality of solid particles and the plurality of liquid droplets containing the plurality of particulates collected from the sampling environment by:

retracting the screen mount assembly through the sample screen housing and the sample screen sampling face:

unlocking the locking arm from the locking arm arrestor body, and manipulating the locking arm, causing expansion of the standoff spring, further causing the sampling screen to be positioned retracted inside of the sample screen housing;

maintaining chain of custody data of samples and sampling data with a plurality of electronic and electrical sampling data collection circuits and a plurality of electronic and electrical sample chain of custody determination circuits; and interfacing collected samples and determined sampling data to analysis platforms and protocols with a plurality of electronic and electrical data analysis interface circuits.

9. The method of SBRC sampling of claim 8, wherein the handheld sampler body includes a battery, a plurality of fans, and a plurality of electrical motors, wherein the plurality of fans and the plurality of electrical motors are communicatively coupled and powered by the battery, forcing air draw through the sampling screen, and causing available samples of contaminants to collect on the sample screen.

10. The method of SBRC sampling of claim 8, wherein the sample screen contains a coating of a sticky substance, causing the sample screen to have an adhesive surface, and wherein the plurality of particulates and the plurality of liquid droplets are adhered to the sample screen by the sticky substance coated on the sample screen.

11. The method of SBRC sampling of claim 10, wherein the sample screen comprises a mesh having holes ranging from about 36 μm holes up to about 152 μm holes, and wherein the sticky substance causing the sample screen to have an adhesive surface can be applied in coated thicknesses selected from a group of thicknesses in a range from about 10 μm thick up to about 20 μm thick and in a range of about 50 μm thick up to about 100 μm thick forming the screen mesh.

12. The method of SBRC sampling of claim 10, wherein the sample screen is selected from a group of sample screens consisting of a stainless steel sticky screen and a polymeric screen and a dome shaped screen and a flat shaped screen, and wherein the sample screen is composed of a fine mesh.

13. The method of SBRC sampling of claim 12, wherein the sample screen composed of the fine mesh is further composed of a plurality of stacked sample screens.

14. A system of sampling of a broad range of chemicals (SBRC), the system comprising:

a handheld sampler body, having a sampling screen sampling face having an at least one sampling cassette; and a sample screen housing residing in the at least one sampling cassette, wherein, the sample screen housing further consists of:

a screen storage body, and a locking arm arrestor body communicatively coupled to a sample access face, wherein, the locking arm arrestor body further consists of:

a screen mount assembly including a draw tube, wherein, the screen mount assembly further consists of:

a locking arm communicatively coupled to a screen cartridge holder, a standoff spring extendably and retractably coupled to the screen cartridge holder, the sampling screen, mounted on the standoff spring, wherein the screen is positioned in one or more positions selected from a group of positions consisting of retractably positioned and extendably positioned in the at least one sampling cassette between a spring stop face and the sample access face, wherein the system further comprises a battery, a plurality of fans, and a plurality of electrical motors, wherein the plurality of fans and the plurality of electrical motors are communicatively coupled to and powered by the battery, wherein the system further comprises a plurality of electronic and electrical sampling data collection circuits, and a plurality of electronic and electrical sample chain of custody determination circuits and a plurality of electronic and electrical data analysis interface circuits, and wherein, when activated by an operator of the system, the system executes a plurality of collecting and sampling the broad range of chemicals operations, as follows:

operations exposing the sampling screen to a sampling environment by a sampling method selected from a group of sampling methods consisting of at least one of:

rotating the sample access face, aligning a sampling port in the sampling access face, wherein the sample access face can only be turned in one direction;

extending the screen mount assembly through the sample screen housing and the sample screen sampling face:

manipulating the locking arm causing compression of the standoff spring, and positioning the locking arm in a locked position in the locking arm arrestor body, wherein the screen mount assembly includes the draw tube, wherein by positioning the locking arm in the locked position, causing the sampling screen to be positioned protruding beyond an outside surface of the sample screen face, and drawing through the draw tube, air from the sampling environment containing a plurality of airborne chemical contaminants causing the plurality of airborne chemical contaminants including aerosol particulates to be collected by and adhered to the sample screen; and extending the screen mount assembly through the sample screen housing and the sample screen sampling face: manipulating the locking arm causing compression of the standoff spring, positioning the locking arm in a locked position in the locking arm arrestor body, and pressing a first surface of the sample screen against a second surface of an object situated in the sampling environment, and collecting, onto the first surface, a plurality of solid particles and a plurality of liquid droplets containing a plurality of particulates from the second surface, wherein positioning the locking arm in the locked position, causes the sampling screen to be positioned protruding beyond an outside surface of the sample screen face; and operations removing the sampling screen from the sampling environment and isolating the plurality of airborne chemical contaminants, the plurality of solid particles and the plurality of liquid droplets containing the contaminants collected from the sampling environment by:

retracting the screen mount assembly through the sample screen housing and the sample screen sampling face:

unlocking the locking arm from the locking arm arrestor body, and manipulating the locking arm, causing expansion of the standoff spring, further causing the sampling screen to be positioned retracted inside of the sample screen housing;

interfacing collected samples and determined sampling data with a plurality of analysis platforms and protocols; and maintaining chain of custody data and chain of custody records of samples and sampling data using a plurality of electronic and electrical sampling data collection circuits and a plurality of electronic and electrical sample chain of custody determination circuits and a plurality of electronic and electrical data analysis and interface circuits.

15. The system of claim 14, wherein the sampling screen contains a coating of a sticky substance, causing the sampling screen to have an adhesive surface, and wherein the plurality of particulates and the plurality of liquid droplets are adhered to the sampling screen by the sticky substance coated on the sampling screen.

16. The system of claim 14, wherein the sample access face is indexed such that the sampling port in the sample access face is aligned in an alignment position selected from a group of alignment positions consisting of alignment with a cylinder in the locking arm arrestor body and the screen storage body and alignment with a blank face of the screen storage body, and wherein one or more o-rings from a plurality of o-rings are mounted on the spring stop face and seal the screen mount assembly from the sampling environment.

17. The system of claim 15, wherein the sampling screen comprises a mesh having holes ranging from about 36 μm holes up to about 152 μm holes, and wherein the sticky substance causing the sampling screen to have an adhesive surface can be applied in coated thicknesses selected from a group of thicknesses in a range from about 10 μm thick up to about 20 μm thick and in a range of about 50 μm thick up to about 100 μm thick forming the mesh of the sampling screen, and wherein the mesh of the sampling screen is a fine mesh.

18. The system of claim 17, wherein the sample screen is selected from a group of sample screens consisting of a stainless steel sticky screen and a polymeric screen and a dome shaped screen and a flat shaped screen.

19. The system of claim 18, wherein the mesh of the sampling screen is composed of a plurality of stacked sampling screens.

20. The system of claim 19, wherein at least one of the plurality of stacked sampling screens is configured between a Direct Analysis in Real Time ambient—ionization outlet and a mass spectrometer inlet, wherein analysis of the contaminants collected is conducted.

\* \* \* \* \*